United States Patent
Jacob et al.

(10) Patent No.: US 10,433,811 B2
(45) Date of Patent: Oct. 8, 2019

(54) SELF-CALIBRATING CT DETECTORS, SYSTEMS AND METHODS FOR SELF-CALIBRATION

(71) Applicant: General Electric Company, Schenectady, NY (US)

(72) Inventors: Biju Jacob, Schenectady, NY (US); Brian David Yanoff, Schenectady, NY (US); Xue Rui, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 216 days.

(21) Appl. No.: 15/591,932

(22) Filed: May 10, 2017

(65) Prior Publication Data

US 2018/0177481 A1    Jun. 28, 2018

Related U.S. Application Data

(60) Provisional application No. 62/438,494, filed on Dec. 23, 2016.

(51) Int. Cl.
    *A61B 6/00*    (2006.01)
    *A61B 6/03*    (2006.01)
    *G01N 23/046*  (2018.01)

(52) U.S. Cl.
    CPC .............. *A61B 6/585* (2013.01); *A61B 6/032* (2013.01); *A61B 6/4233* (2013.01); *A61B 6/4241* (2013.01); *G01N 23/046* (2013.01); *G01N 2223/303* (2013.01); *G01N 2223/33* (2013.01)

(58) Field of Classification Search
    CPC ......... A61B 6/14; A61B 6/4064; A61B 6/032; A61B 6/035; A61B 6/4007; A61B 6/4266; A61B 6/4435; A61B 6/4241; A61B 6/585; A61B 6/4233; G01N 2223/303; G01N 2223/33; G01N 23/046
    See application file for complete search history.

(56) References Cited

U.S. PATENT DOCUMENTS

| | | |
|---|---|---|
| 4,991,189 A | 2/1991 | Boomgaarden et al. |
| 5,131,021 A | 7/1992 | Gard et al. |
| 5,430,785 A | 7/1995 | Pfoh et al. |
| 5,450,461 A | 9/1995 | Hsieh |
| 5,473,656 A | 12/1995 | Hsieh et al. |
| 5,949,842 A | 9/1999 | Schafer et al. |
| 6,094,469 A | 7/2000 | Dobbs et al. |
| 6,148,057 A | 11/2000 | Urchuk et al. |

(Continued)

OTHER PUBLICATIONS

Grimmer, Rainer, et al.; "A new method for cupping and scatter precorrection for flat detector CT", Nuclear Science Symposium Conference Record (NSS/MIC), 2009 IEEE, pp. 3517-3522, Oct. 24-Nov. 1, 2009, Orlando, FL.

(Continued)

*Primary Examiner* — Chih-Cheng Kao (57) ABSTRACT

The present approach relates to self-calibration of CT detectors based on detected misalignment of the detector and X-ray source. The present approach make the detector more robust to changes against temperature and focal spot movements. The diagnostic image generated by energy resolving calibrated response signals is able to present enhanced features compared to conventional CT based diagnostic images.

19 Claims, 10 Drawing Sheets

(56) References Cited

U.S. PATENT DOCUMENTS

| | | | |
|---|---|---|---|
| 6,359,955 B1* | 3/2002 | Nukui | A61B 6/032 378/19 |
| 7,016,456 B2 | 3/2006 | Basu et al. | |
| 7,086,780 B2 | 8/2006 | Wu et al. | |
| 7,801,264 B2 | 9/2010 | Wu et al. | |
| 7,825,370 B2 | 11/2010 | Ikhlef et al. | |
| 8,774,350 B2 | 7/2014 | Tsubota et al. | |
| 2012/0177174 A1 | 7/2012 | Ikhlef et al. | |
| 2014/0233694 A1* | 8/2014 | Wang | A61B 6/583 378/5 |
| 2016/0095564 A1* | 4/2016 | Kato | A61B 6/52 378/19 |
| 2016/0113603 A1 | 4/2016 | Schirra et al. | |
| 2016/0206255 A1* | 7/2016 | Gagnon | A61B 6/4241 |
| 2019/0008474 A1* | 1/2019 | Sjolin | A61B 6/587 |

OTHER PUBLICATIONS

Zhao, Wei, et al.; "Patient-specific scatter correction for flat-panel detector-based cone-beam CT imaging", Physics in Medicine and Biology, vol. 60, Issue: 3, Jan. 16, 2015.

* cited by examiner

SELF-CALIBRATING CT DETECTORS, SYSTEMS AND METHODS FOR SELF-CALIBRATION

CROSS-REFERENCE TO RELATED APPLICATION

This application claims priority to and the benefit of Provisional Application No. 62/438,494, entitled "SELF-CALIBRATING CT DETECTORS, SYSTEMS AND METHODS FOR SELF-CALIBRATION", filed Dec. 23, 2016, which is herein incorporated by reference in its entirety.

BACKGROUND

Embodiments of the present specification relate generally to computed tomography (CT), and more particularly to self-calibrating CT detectors, systems and methods for self-calibration.

In an imaging system, such as a computed tomography (CT) imaging system, a fan shaped X-ray beam is emitted towards an object such as a patient or a piece of luggage to image a region of interest in the object. The beam is typically attenuated by the object. Subsequently, the attenuated beam is incident on a CT detector having an array of detector elements. In response to the attenuated beam, the detector elements of the array generate respective electrical signals representative of internal information of the object. These electrical signals are processed by a data processing unit to generate an image representative of the region of interest in the object.

Typically, the array of detector elements is constructed to have a standard response for all detector elements. However, there may be variations among the responses of the detector elements. Numerous other factors such as, but not limited to, geometric parameters of the imaging system, detector gain, shading effects of auxiliary components, such as anti-scatter grids or collimators, of the detectors, may influence the response from the detector elements in different ways. In particular, during usage, and/or over time, detector response may change due to variations in temperature, tube spectrum, and gantry movement. It is desirable to calibrate the CT detector to at least partly compensate for degradation of image quality caused due to variation in detector response.

Typically, a calibration is performed before the shipment of the equipment, at the time of installation of the imaging system by the end user (e.g., hospital radiology staff) or by a field engineer employed by the system manufacturer. Calibration values for some or all of the detector elements are computed from the calibration. Subsequently, the calibration values are applied to the electrical signals generated by the detector elements during operation of the imaging equipment. The calibration may be repeated periodically and/or during imaging system modification or maintenance events to regenerate the calibration values.

However, in current systems, there are no mechanisms to detect and correct the variations that occur "during" the operation. This, combined with the fact that calibrations are often not performed as often as may be needed (due to the time consuming nature of existing calibration techniques) results in less effective calibration values continuing to be used for periods longer than may be desirable.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one implementation, a method is provided for calibrating an energy resolving computed tomography (CT) system comprising an X-ray source and a pixelated detector. In accordance with aspects of this implementation, for each respective segment of a detector element comprising a plurality of segments, a respective response signal is acquired. Each response signal comprises a plurality of photon counts each corresponding to a different energy bin of the respective segment. For the detector element, a first photon count for an energy bin of a first segment and a second photon count for the same energy bin of a second segment are determined. The first segment and the second segment are vertically offset within the respective detector element. A photon count ratio is determined based on the first photon count and the second photon count. A misalignment angle of the detector element with reference to the X-ray source is determined based on the photon count ratio. A plurality of gain factors are determined for the plurality of segments of the detector element based on the photon count ratio and the misalignment angle. A corrected spectrum for the detector element is determined using the plurality of gain factors and the response signals.

In a further implementation, a computed tomography (CT) imaging system is provided. In accordance with aspects of this implementation, the CT imaging system includes a radiation source configured to emit radiation and a pixelated detector configured to generate signals in response to the emitted radiation. The pixelated detector comprises a plurality of detector elements, each detector element comprising a plurality of segments offset in the direction of radiation propagation. The CT imaging system further includes a readout channel for each segment of each detector element. Each readout channel, during operation, generates a photon count for each bin in a plurality of energy bins. The CT imaging system further includes a calibration sub-system configured to, based upon the photon counts for a first segment and a second segment of a respective detector element: determine a first photon count for an energy bin of the first segment and a second photon count for the same energy bin of the second segment, wherein the first segment and the second segment are vertically offset within the respective detector element; determine a photon count ratio based on the first photon count and the second photon count; determine a misalignment angle of the detector element with reference to the radiation source based on the photon count ratio; determine a plurality of gain factors for to the plurality of segments of the detector element based on the photon count ratio and the misalignment angle; and determine a corrected spectrum for the detector element using the plurality of gain factors and the response signals. The CT imaging system further includes an image reconstruction unit configured to generate an output image using the respective corrected spectra of some or all of the detector elements.

In an additional implementation, one or more non-transitory computer-readable media storing processor-executable instructions are provided. In accordance with aspects of this implementation, the instructions, when executed by one or more processors, cause the one or more processors to performs acts comprising: for each respective segment of a detector element comprising a plurality of segments, acquire a respective response signal, wherein each response signal comprises a plurality of photon counts each corresponding to a different energy bin of the respective segment; for the detector element, determine a first photon count for an energy bin of a first segment and a second photon count for the same energy bin of a second segment, wherein the first segment and the second segment are vertically offset within the respective detector element; determine a photon count ratio based on the first photon count and the second photon count; determine a misalignment angle of the detector element with reference to an X-ray source based on the photon count ratio; determine a plurality of gain factors for the plurality of segments of the detector element based on the photon count ratio and the misalignment angle; and determine a corrected spectrum for the detector element using the plurality of gain factors and the response signals.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context or image processing field where a set or type of acquired data undergoes a reconstruction process to generate an image or volume.

Embodiments of the present disclosure relate to self-calibrating computed tomography (CT) detectors, self-calibrating CT systems, and methods for self-calibration of a detector. In particular, the systems and methods disclosed herein facilitate at least partial correction of misalignment of an X-ray beam with respect to a detector element in an energy-resolving, photon-counting CT imaging system.

Further, in current systems there are typically no mechanisms to detect and correct the variations that occur "during" operation. The present approach allows detection of misalignment of a detector element (i.e., pixel) in real-time with respect to the X-ray focal spot. The approach further includes algorithmic correction of the error in the output spectrum caused by the misalignment.

As discussed herein, in certain implementations, the energy resolving CT imaging system includes a detector having vertically segmented detector elements from which signals are readout from different depths of a respective segmented detector element. In operation, a self-calibrating CT detector receives a plurality of response signals from the segmented detector elements. As discussed herein, these signals are used to determine a misalignment angle of a detector element (i.e., a pixel) with respect to the X-ray source. In one implementation, this information is used to determine gain factors to correct the errors in a spectral response caused by the misalignment and subsequently the corrected spectrum of the pixel.

More generally, and as discussed herein, a self-calibrating CT detector is used to generate calibration values that can be used to adjust one or more operating parameters of a CT imaging system to generate a quality imaging signal and/or to process the imaging signal generated by the CT imaging system to correct or enhance the signal quality. As used herein, the terms "pixel", and "segmented detector" are used equivalently to denote detector elements of a pixelated detector. As used herein, the term "gain factor" refers to a gain value that is applied to a response signal of a segmented detector. Further, as used herein, the term "scattering signal" refers to a component of a detector signal representative of X-ray photons that have undergone a directional change in their flight between the X-ray source and detector. Furthermore, the term "pile-up" refers to a detector response exhibiting a saturating response when the density of X-ray photons increases beyond a threshold value. As used here, the term "channel" is used equivalently and interchangeably to refer to a combination of a plurality of segments and corresponding read-out electronics of a detector, where the combination is configured to generate a response signal. The term "response" refers to a response signal obtained from a segmented detector. In the case of the segmented detector, the response signal includes a plurality of photon counts corresponding to a plurality of energy bins, e.g., different discrete energy ranges corresponding to the energy of a respective X-ray photon. Each of the photon count values among the plurality of photon counts is generated by a photon counter associated with a segment of the segmented detector. Further, the term "count ratio" refers to a ratio of photon counts corresponding to two segments of the segmented detector. The term "normal count ratio" refers to a photon count ratio of a segmented detector for a detector that is perfectly aligned with the direction of travel of the X-ray beam. The term "measured count ratio" refers to a photon count ratio of two response signals corresponding to two segments of the segmented detector, obtained from measurements. In one embodiment, the measured count ratio refers to a ratio of photon counts corresponding to an energy bin among the plurality of energy bins. The terms "angular position" and "view angle" are used equivalently and interchangeably throughout this application to refer to an angular orientation of a radiation source or a detector.

Figure 1A:
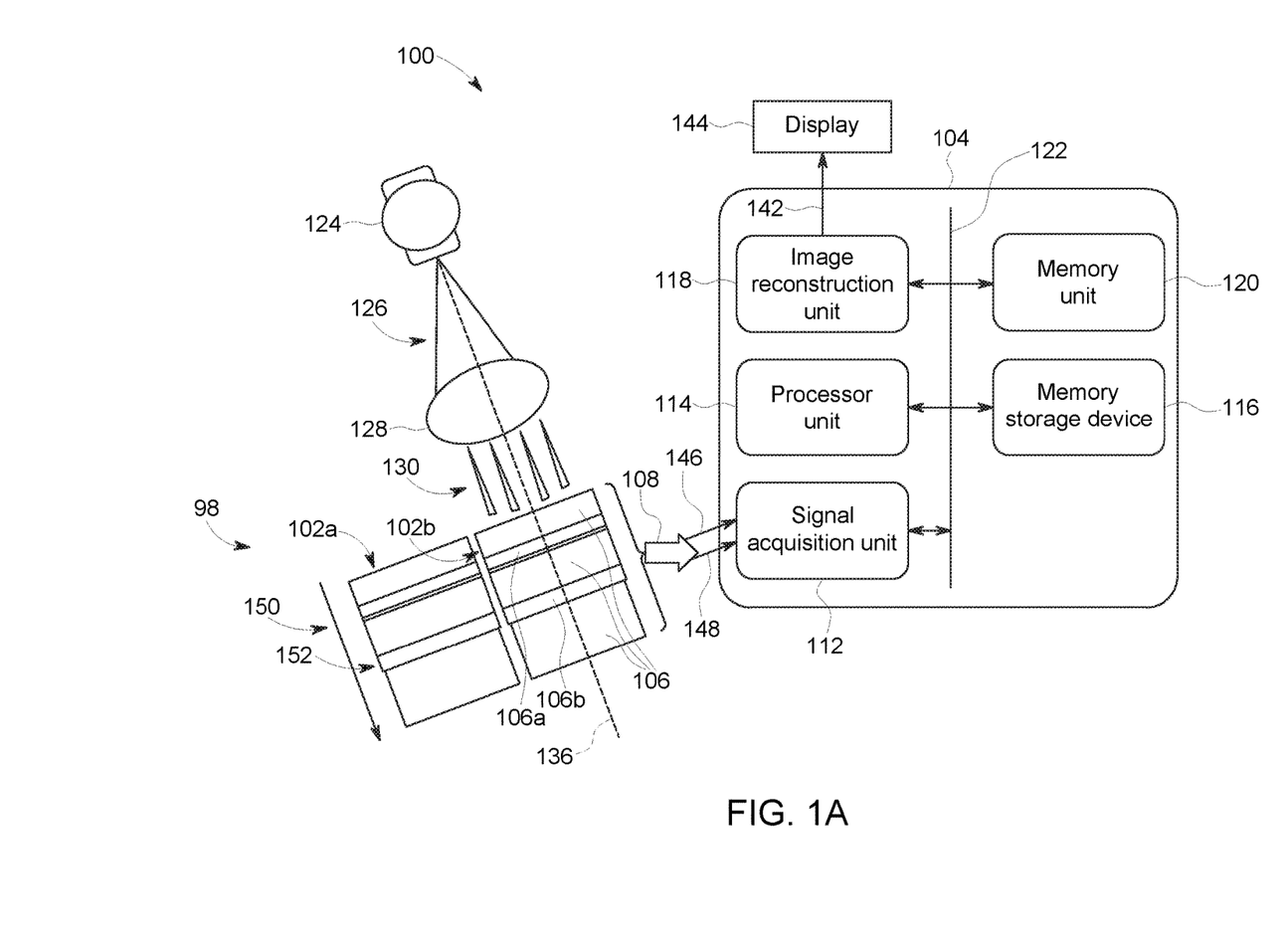
FIGS. 1A and 1B are block diagram representations of a self-calibrating computed tomography (CT) system illustrating an aligned geometry (FIG. 1A) and a mis-aligned geometry (FIG. 1B), in accordance with aspects of the present disclosure.
Figure 1B:
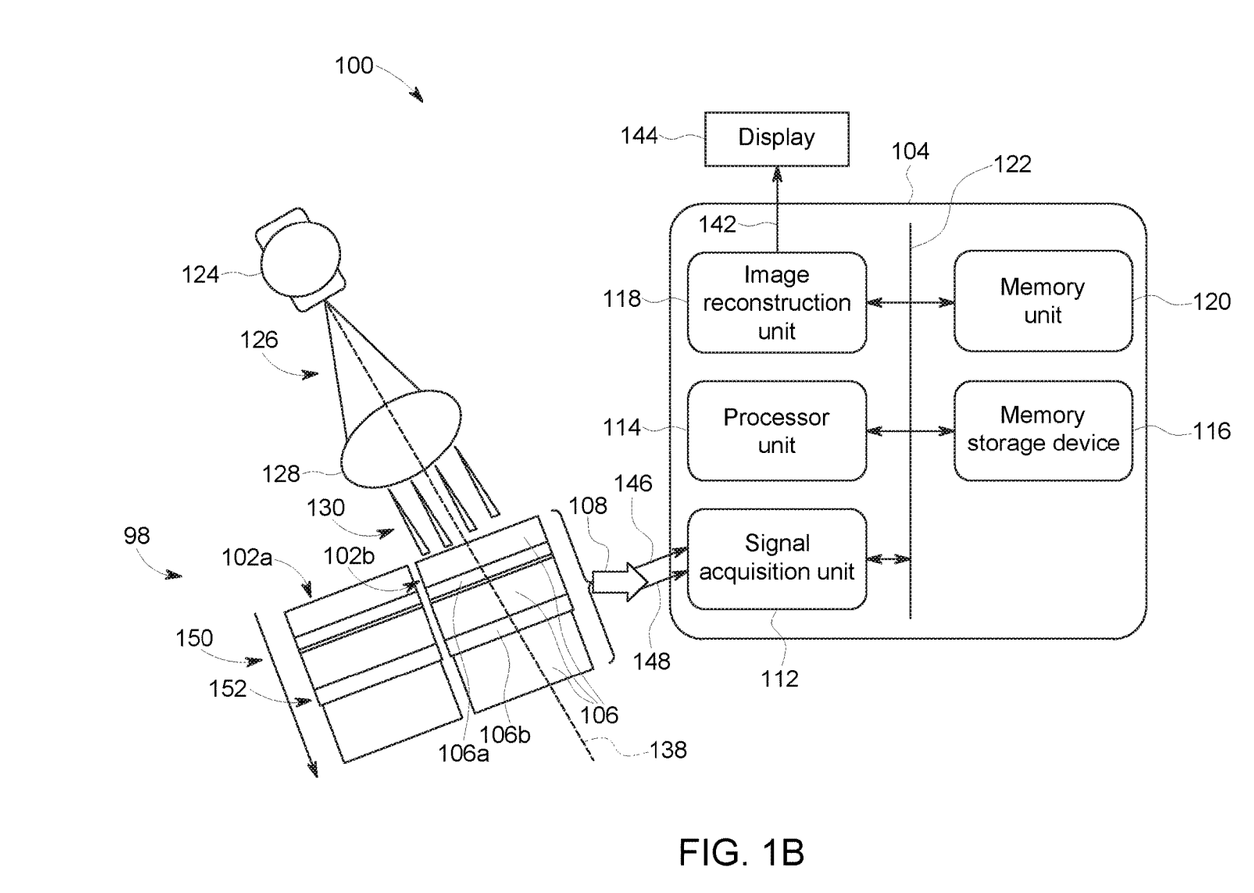

FIGS. 1A and 1B are block diagram representations of an imaging system 100, such as a self-calibrating computed tomography (CT) system, in accordance with aspects of the present specification. FIG. 1A depicts the CT imaging system 100 in an aligned geometry while FIG. 1B depicts the CT imaging system in a mis-aligned geometry. As shown in the figures, imaging system 100 includes a radiation source 124 configured to emit a radiation signal 126 and impinging an object 128 to generate a plurality of intensity signals 130. In one embodiment, the radiation source 124 is an X-ray source, such as an X-ray tube. The object 128 may be an organ of a subject to be examined or a piece of luggage to be scanned. The imaging system 100 also includes a pixelated detector 98 having a plurality of detector elements in the form of a plurality of pixels 102a, 102b, typically arranged in an m x n array.

In one embodiment, the pixelated detector 98 is an energy-resolving photon counting CT detector, such as may have improved contrast-to-noise ratio and the ability to perform K-edge imaging. Such an energy-resolving, photon-counting detector may be fabricated using semiconductor materials as the active material, such as cadmium telluride/cadmium zinc telluride (CdTe/CZT) or silicon. In certain implementations discussed herein, a detector 98 employing segmented silicon strips as the detector elements (i.e., pixels 102) is described.

By way of example, turning to the figures, each of the plurality of pixels 102a, 102b includes a detector element (such as a silicon strip) having a plurality of segments 106 disposed at a plurality of depths with respect to the path of the emitted X-rays with respect to the surface of the pixels 102 facing the source 124. As used herein, the direction traveled by the X-rays (i.e., the direction of X-ray propagation) with respect to the source-facing surface of the pixels 102 may be denoted as "vertical" and/or may be construed as corresponding to a depth dimension, hence such a segmented detector element may be described as vertically segmented.

As may be appreciated, in the context of a pixelated detector 98 for use in CT, the detector 98 includes a plurality of such pixels 102 in two dimensions for each angular position among the multiple angular positions at which X-rays are incident on the detector 98. The plurality of vertical segments 106 within a pixel 102 may have different heights and/or thicknesses and generate response signals that may be used for reducing effect of artifacts in signals generated by the pixels 102 of the pixelated detector 98.

The pixelated detector 98 is configured to receive the plurality of intensity signals 130 and generates a plurality of response signals 108 from the plurality of segments 106 for each pixel of the plurality of pixels 102. The plurality of response signals 108 is representative of imaging information from a region of interest of the object 128. The plurality of response signals 108 constitute energy resolving spectral information. In one embodiment, each of the plurality of response signals 108 includes a plurality of photon counts corresponding to a plurality of energy bins. Each photon count among the plurality of photon counts is indicative of a number of X-rays having energy corresponding to a given energy bin. Hence, a response signal may be generated for each pixel and energy bin of that respective pixel so as to provide, for a given readout interval, a number of photon counts for each energy bin at each spatial location corresponding to a respective pixel 102.

Thus, in this example, the pixelated detector 98 generates information corresponding to the pixels 102 in the form of a plurality of response signals 108. In the depicted example, the plurality of intensity signals 130 corresponds to one angular position of the radiation source 124 and detector 98. In a CT system, the radiation source and detector 98 rotate about the object 128 to acquire X-ray transmission data. Thus, in a real-world implementation, the imaging system 100 is configured to generate a plurality of intensity signals 130 corresponding to each of the plurality of angular positions (e.g., 360°, 180°+a fan beam angle ($\alpha$), and so forth) covering an entire scanning area of interest.

The pixelated detector 98 is configured to generate an artifact free response for the plurality of intensity signals 130 corresponding to a particular angular position when the pixelated detector 102 is aligned with the radiation source 124, as shown in FIG. 1A. However, as shown in FIG. 1B, a misalignment between the X-ray source 124 and a given pixel 102 may introduce an error in the plurality of response signals 108. This is illustrated in FIGS. 1A and 1B, with FIG. 1B having a first transmission line 138 illustrating an unaligned X-ray transmission relative to a second transmission line 136 (depicted in FIG. 1B) illustrating X-ray transmission when the source 124 and detector 98 are properly aligned (i.e., along an axis of the pixels 102). Further, the plurality of response signals 108 include a plurality of scattering signals generated from X-ray photons being deflected when traveling between the source 124 and detector 98. The plurality of response signals 108 may also include a plurality of corrupted signals generated from pile-up response with respect to one or more pixels 102, whereby response at a given pixel is saturated and not indicative of the actual X-ray incidence at the pixel.

The imaging system 100 further includes an image reconstruction unit configured to generate a diagnostic image 142. In one embodiment, the diagnostic image 142 is obtained using image reconstruction techniques applied to the plurality of calibrated signals obtained from the plurality of pixels 102. In one embodiment, the diagnostic image 142 is a calibrated CT image displayed on a display device 144 for assisting a medical practitioner.

As noted above, the pixel 102 of the detector 98 are vertically segmented, and may in one implementation be segmented silicon strips. By way of example, in the illustrated embodiment each pixel 102 is segmented into a plurality of segments 106, such as a first segment 106a disposed at a first depth represented by reference numeral 150 and a second segment 106b disposed at a second depth represented by reference numeral 152. In one such example the first segment 106a is configured not to saturate (such as due to having a limited thickness that will not saturate under imaging conditions. In this example, the non-saturating first segment 106a is designed to generate a response signal that is not affected by pile-up artifact effects. The non-saturating response is generated by the first segment 106a in response to the plurality of intensity signals 130. In the depicted implementation, the second segment 106b is also designed to be a non-saturating detector segment at a different depth, e.g., beneath the first segment with respect to the direction traveled by the X-ray beam.

The depicted example of an imaging system 100 further includes a calibration sub-system 104 having a signal acquisition system 112, a processor unit 114, an image reconstruction unit 118, a memory unit 120, and a memory storage device 116 interconnected with each other by a communications bus 122. The imaging system 100 also includes a display communicatively coupled to the image reconstruction unit 118. In one embodiment, the calibration sub-system 104 is configured to receive the plurality of response signals 108 and generate a diagnostic image 142. The diagnostic image 142 is a calibrated image generated based on the corrected spectrum signals corresponding to the plurality of pixels 102 of the pixelated detector 98.

Figure 2:
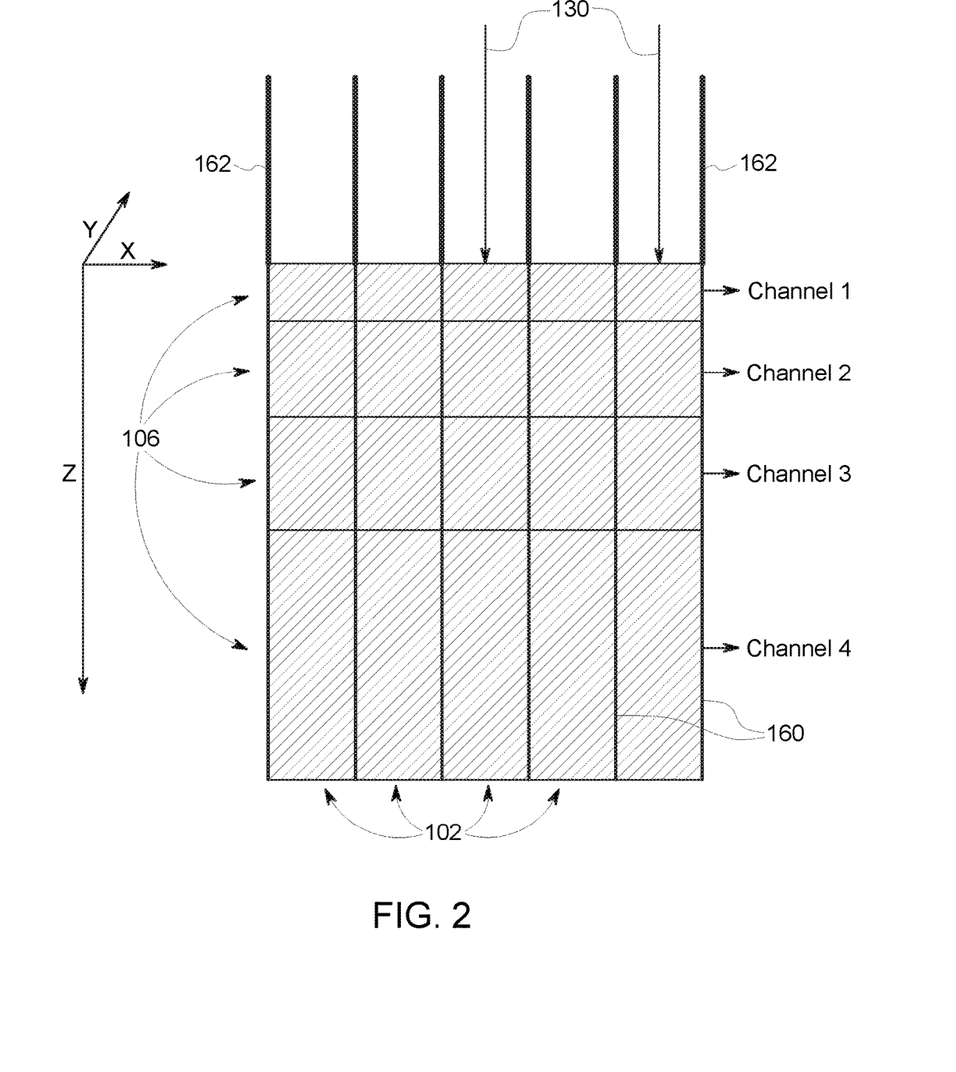
FIG. 2 depicts a side-sectional view of a segmented pixelated detector, in accordance with aspects of the present disclosure.

With the preceding in mind, FIG. 2 depicts the geometry of the detector 98 as a sectional view showing vertically segmented segments 106 of each pixel 102. In the frame of reference shown, the detector elements in the form of pixels 102 are segmented along the direction of X-ray propagation (i.e., the Z-axis) and the segments 106 at different depths are of different thicknesses. For example, in the depicted example the segments 106 increase in thickness as their depth in the z-direction increases. In accordance with present approaches, the segments at different depths each correspond to a different readout channel. Thus, in this example, there are four segments 106 (i.e., readout channels) for any given pixel 102. As discussed in greater detail below, each segment 106 of each pixel 102 may be readout by a given readout channel into a plurality of energy ranges (i.e., energy bins) to generate a photon count for each energy bin for a given readout interval or period.

With this in mind, and turning back to FIG. 1, in one embodiment, computing the corrected spectrum includes processing the plurality of response signals 108 using one or more algorithms or routines executed on the processor unit 114. In one such approach, the processor unit 114 is configured or programmed to select a first photon count 146 from a first response signal and a second photon count 148 from a second response signal generated by the same detector element (i.e., pixel 102). In this example, the first photon count 146 and the second photon count 148 correspond to a same energy range (e.g., energy bin) among a plurality of energy bins associated with their respective segments. The processor unit 114 is also configured or programmed to determine a photon count ratio based on the first photon count 146 and the second photon count 148. Further, the processor unit 114 is also configured or programmed to determine a misalignment angle of the respective detector element (used to generate the respective photon counts) with reference to the X-ray source 124 based on the first photon count 146 and the second photon count 148. The processor unit 114 is further configured or programmed to determine gain factor for each segment of the respective detector element based on the photon count ratio and the misalignment angle. The corrected spectrum corresponding to a respective pixel 102 is computed based on gain factors for the segments of the respective pixel and the plurality of response signals 108.

Turning back to FIG. 2, in one embodiment, the pixels 102 are separated laterally by anti-scatter Tungsten plates 160 (e.g., a 20 μm sheath of tungsten) along the X-axis. The tungsten plates 160 help to prevent internal scatter within the detector. The pixels 102 are, in one implementation, separated along the Y-axis pixels 102 by electrical bias. By way of example, an implementation of a pixel 102 may measure ~0.4 to 0.5 mm in the X-dimension and 0.5 mm in the Y-dimension and have an absorption length between 30 mm to 80 mm (such as approximately 30 mm or 60 mm) in the Z-dimension. In one implementation, the detector strip corresponding to a pixel 102 may be divided into nine segments 106, with variations in the segmentation length so that approximately uniform count rates are expected along the depth of the detector. That is the increased thickness of deeper segments 106 may be designed so as to have uniform count rates at each segment 106 within a pixel (i.e., taking into account absorption of X-ray photons by higher segments in the pixel 102). In addition, as shown in FIG. 2, in some embodiments, a one- or two-dimensional anti-scatter collimator 162 may be provided at the X-ray facing surface of the detector 98.

Figure 3:
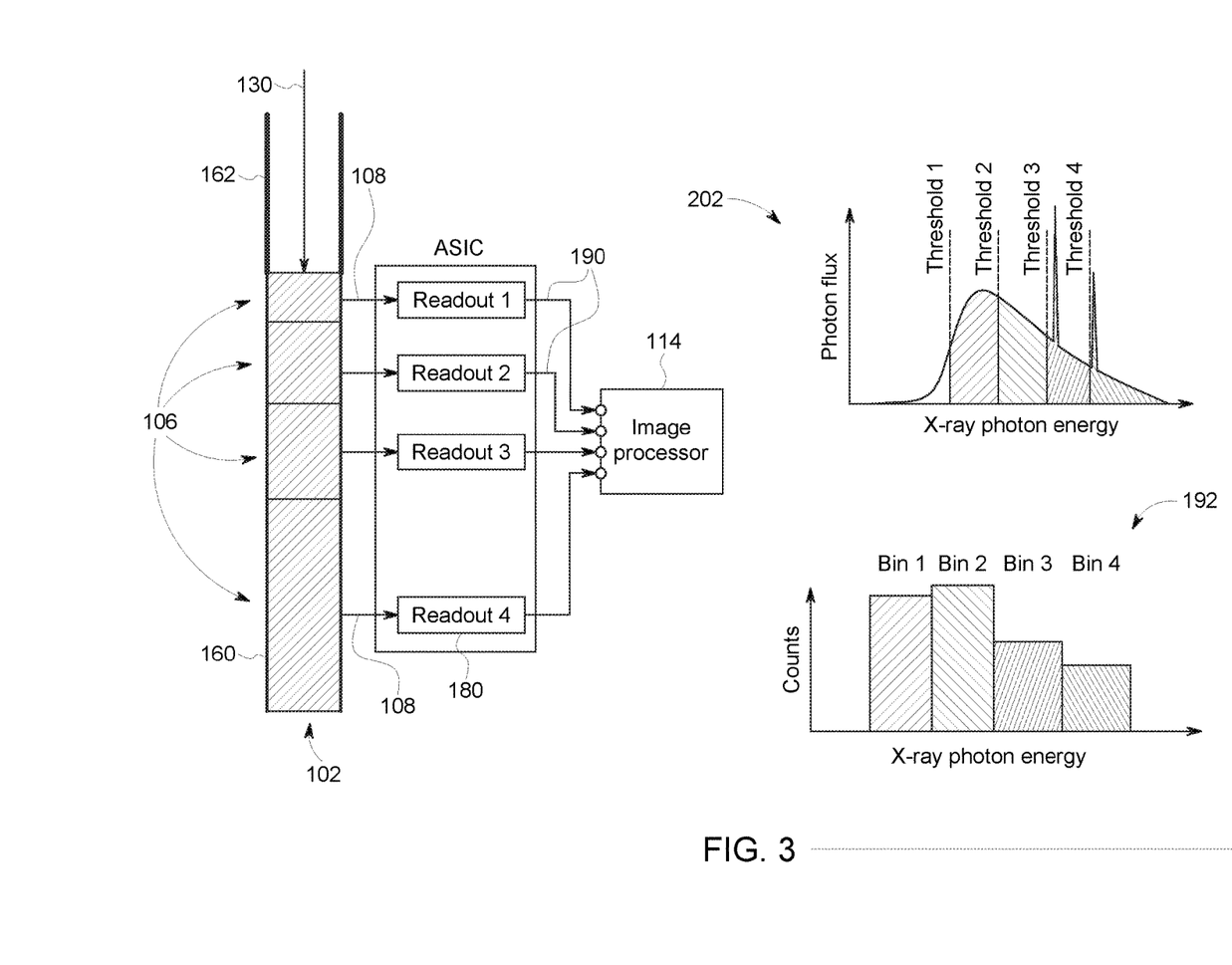
FIG. 3 depicts the readout chain of a detector, in accordance with aspects of the present disclosure.

With the preceding in mind, FIG. 3 depicts the readout chain of an energy-resolving, photon-counting detector 98 having vertically segmented silicon strip detector elements (i.e., pixels 102) as discussed herein. In this example, the post-patient X-ray 130 has both primary and scatter components. The aggregate of the post-patient X-rays 130 correspond to an input or incident spectrum 202 that passes through the anti-scatter grid 162 before it hits the detector 98, an element 102 of which is shown in FIG. 3. The incident spectrum 202 is represented as a graph of photon flux as a function of X-ray photon energy. A significant fraction of the incoming X-ray photons are absorbed in the various segments 106 in the detector elements 102 of the detector.

Figure 4:
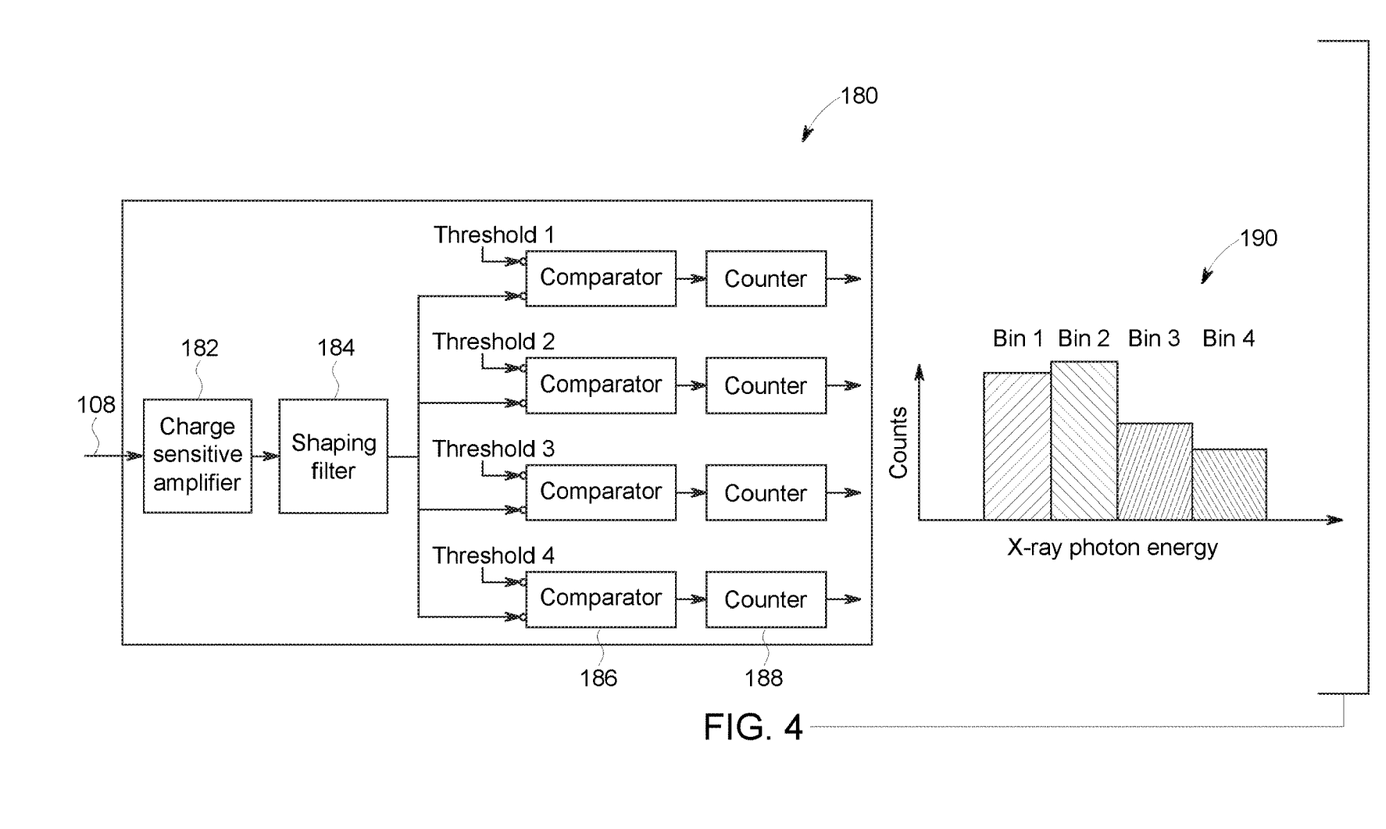
FIG. 4 depicts a readout channel of a segment of a detector element, in accordance with aspects of the present disclosure.

The resulting detector response signals 108 for each respective segment 106 of a pixel 102 are fed into or acquired by readout circuitry, here represented as ASIC channels 180 (i.e., Readout 1, Readout 2, and so forth), such that each segment 106 has a corresponding readout channel. As shown in FIG. 4, which depicts an example of a respective readout channel 180, the acquired signals 108 for a given segment 106 of a pixel 102 are amplified (charge sensitive amplifier 182), conditioned (shaping filter 184), discriminated in energy (comparators 186 with corresponding energy bin thresholds) and digitized (energy bin counters 188) to generate the energy resolved spectral response 190 for each segment 102, as shown by the example ASIC channel 180 of FIG. 4. Thus, an ASIC channel 180 generates a plurality of counts representative of the X-ray response signal, with the counts sorted into a plurality of energy ranges (i.e., bins) defined by a plurality of thresholds.

As will be appreciated, spectral output for each segment 106 of a respective pixel 102 is different. By way of example, the intensity (count rate) is higher for segments 106 closer to the surface of the pixel 102 facing the X-ray source as the X-ray attenuation is an exponential function of the depth of interaction. The shape of the spectrum 180 for each segment is also different, with segments closer to the surface having relatively larger contributions from the low-energy X-ray photons compared to the lower segments, which correspondingly have greater contributions from high-energy X-ray photons.

Turning back to FIG. 3, the energy resolved spectral outputs 190 from each segment 106 of a respective pixel 102 are combined, such as at image processor 114, to generate an energy-resolved pixel output spectrum 192. By way of example, in one implementation, the final spectrum 192 for a given pixel 102 is composed of the sum of spectra from each segment 106 of the pixel:

$$\text{Final Spectrum, } s(E_j) = \sum_{i=1}^{Nsegment} s_i(E_j), \quad (1)$$

where $s(E_j)$ is the pixel output spectrum, $s_i(E_j)$ is the spectrum from i-th segment.

As discussed in greater detail below, based on the energy-resolved output spectrum 192 for a pixel 102, signals generated by the respective readout channels 180 for each segment 106 of that pixel 102 may be gain-corrected or adjusted based on the derived spectral information. For example, current signal generated for a given segment 106 in response to the incident spectrum 202 may be adjusted by some determined gain adjustment (e.g., by addition or subtraction) to derive a gain-corrected signal to generate individually calibrated response signals at the segment level for each pixel 102.

By way of example, an adder may be used to sum up the individual calibrated response signals to generate a corrected spectrum for a pixel 102 having a plurality of segments 106. The corrected spectrum 192 includes a plurality of photon counts corresponding to the plurality of energy bins. Similarly, pixel values from the aggregated pixels 102 of the detector 92 that are corrected in this manner may be used to generate a diagnostic image. In one embodiment, the calibration sub-system 104 of FIG. 1 automatically determines the plurality of gain factors or adjustments for the respective plurality of pixels 102 in a real-time manner to provide calibrated signals used to generate the diagnostic image 142.

Figure 5:
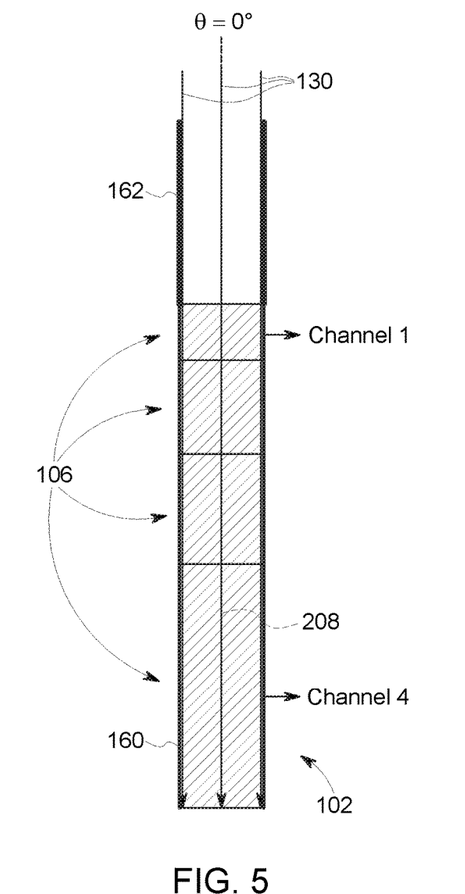
FIG. 5 depicts an aligned detector element, in accordance with aspects of the present disclosure.
Figure 6:
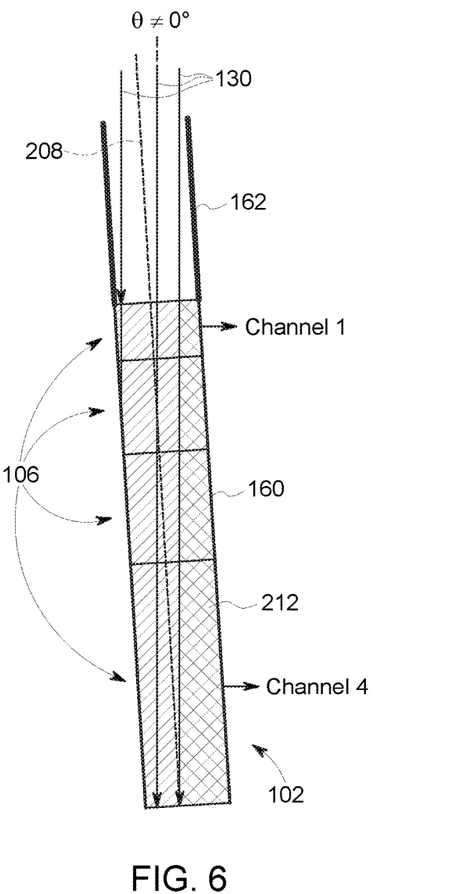
FIG. 6 depicts a misaligned detector element, in accordance with aspects of the present disclosure.

With the preceding in mind, FIGS. 5 and 6 illustrate the geometry of a vertically segmented detector element (i.e., pixel 102) with respect to an X-ray focal spot direction in more detail. As will be appreciated, when the detector 98 is perfectly aligned, as shown in FIG. 5, the primary X-ray beam 130 is normally incident on the pixel segments 106 (i.e., the X-ray beam 130 propagates in a direction parallel to or coincident with the longitudinal axis 208 of a detector element 102). That is, when aligned, the axis 208 of the detector element 102 is at a zero tilt angle θ with respect to the incident X-ray beams 130. In this aligned geometry, the X-ray beam 130 generates the maximum response from all the segments 106 within a given pixel 102.

Conversely, when the detector element 102 and focal spot are misaligned (i.e., have a non-zero tilt angle θ), as shown in FIG. 6, fewer X-ray photons 130 are absorbed in the pixel segments 106 due to the shadowing effects of both the anti-scatter grid 162 and intra-pixel tungsten separator plates 160, with the deeper segments generating disproportionately fewer counts due to these shadowing effects. This is illustrated in FIG. 6 by shaded region 212, which increases in terms of proportional area as depth within the pixel 102 increases. This unequal decrease in counts in different segments results in the corruption of output spectrum 192 of the segmented pixel 102.

With the preceding in mind, the present approach detects the misalignment of a detector element, i.e., pixel 102, with respect to an X-ray focal spot. Such detection can occur in real-time, such as during a clinical scan operation. As discussed in greater detail below, focal spot misalignment, when detected, can be corrected or compensated for, such as via the algorithm discussed herein, to correct for the error in the output spectrum caused by the misalignment. Thus, the present approach: (1) estimates the misalignment angle θ from the responses of different segments 106 in a vertically-segmented pixel 102; and/or (2) corrects an error in an output spectrum 192 caused by misalignment of a vertically-segmented pixel 102 and an X-ray focal spot.

In particular, with respect to the detection of misalignment angle θ using a vertically-segmented detector element, the multiple segments along the depth of X-ray interaction can be exploited to estimate the misalignment angle θ in a respective detector element (i.e., pixel 102). By way of example, and turning to FIG. 7, two vertical segments 106A, 106B offset by a distance L are shown. In the depicted example, the segments are relatively narrow, however the approach can be configured to work for any two segments 106 in the detector element 102.

Figure 7:
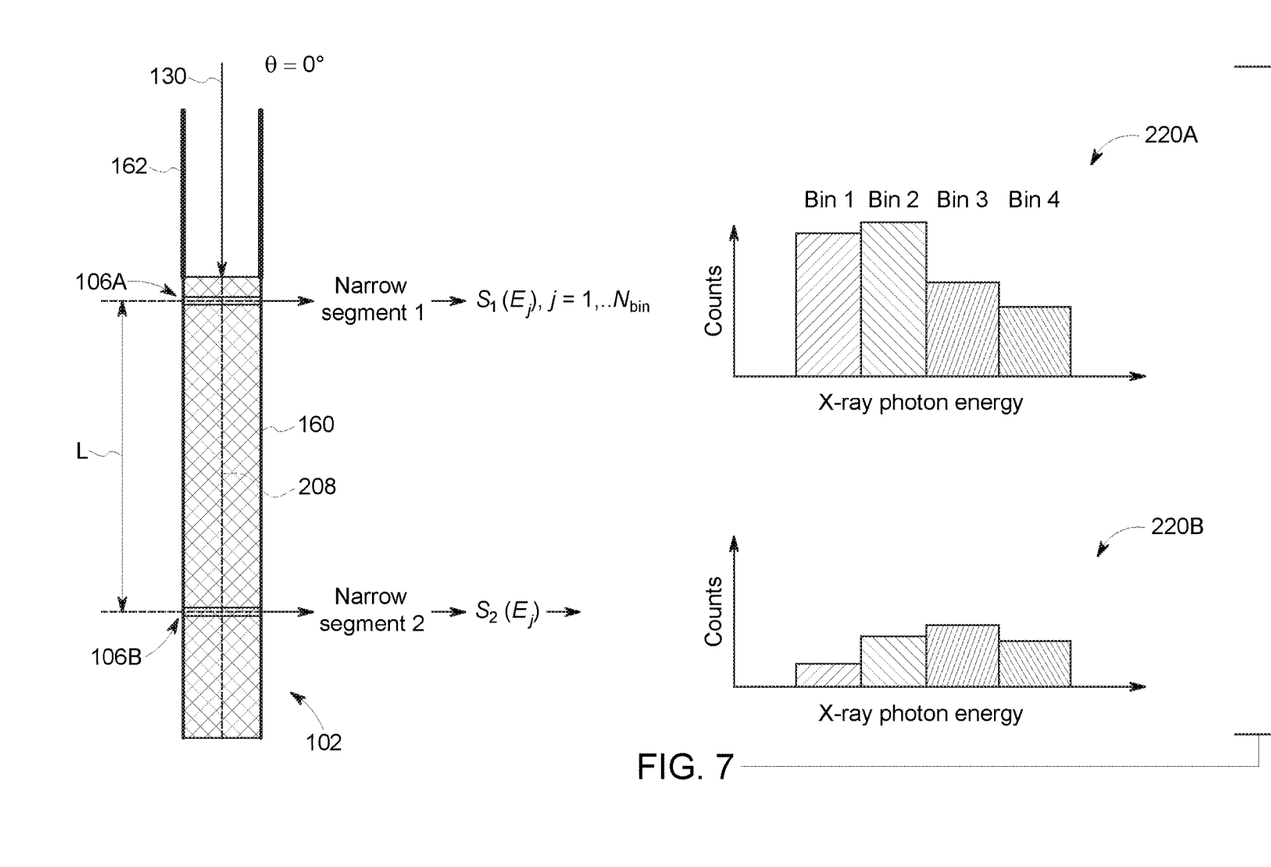
FIG. 7 depicts a detector element sampled at offset segments and corresponding spectrum for each segment, in accordance with aspects of the present disclosure.

For this arrangement, for a focally aligned detector (θ=0°), as shown in FIG. 7, the spectrum 220B at narrow segment 2 ($s_2(E_j)$) is related to the spectrum 220A at segment 1 ($s_1(E_j)$) by the X-ray attenuation factor, $e^{-\mu(E_j)L}$ where $\mu(E)$ is the linear attenuation coefficient of the material and L is the separation between the two segments.

$$s_2(E_j) = s_1(E_j) \cdot e^{-\mu(E_j)L} \text{ or} \quad (2)$$

$$\frac{\sum_j s_1(E_j) \cdot e^{-\mu(E_j)L}}{\sum_j s_2(E_j)} = 1 \quad (3)$$

Figure 8:
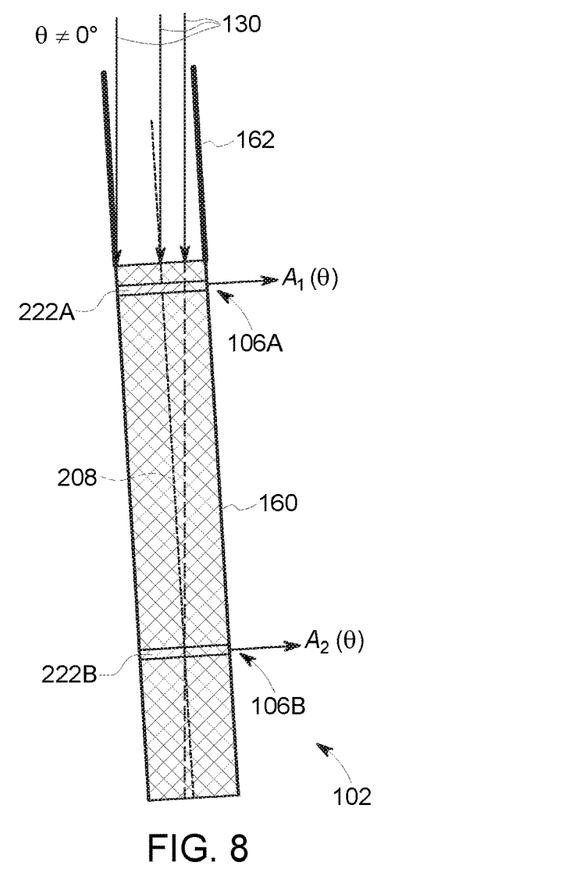
FIG. 8 depicts a misaligned detector element, in accordance with aspects of the present disclosure.

However, turning to FIG. 8, when the detector element 102 is misaligned with respect to the X-ray focal spot (i.e., θ≠0°) the above equality no longer holds and there is an additional gain factor, g(θ), in the relation between the spectra 220A and 220B of the segments 106A and 106B. This is due to the different amount of overlap between the X-ray beam and the detector segments (illustrated by the shaded regions 222A, 222B in FIG. 8). The functional relation between the spectra 220 is modified to be:

$$\frac{s_1(E_j) \cdot e^{-\mu(E_j)L}}{s_2(E_j)} = g(\theta) = \frac{A_1(\theta)}{A_2(\theta)} \quad (4)$$

With respect to g(θ), this term can be estimated from measured counts ($s(E_j)$) as follows:

$$R = g(\theta) = \frac{\sum_{j=1}^{N_{bins}} s_1(E_j) \cdot e^{-\mu(E_j)L} \Delta E_j}{\sum_{j=1}^{N_{bins}} s_2(E_j) \Delta E_j} \quad (5)$$

where $\Delta E_j$ is the width of j-th energy bin. With the preceding in mind, the algorithm for estimating the misalignment angle θ may initially involve deriving the tilt angle response function g(θ) based on the detector geometry:

$$g(\theta) = \frac{A_1(\theta)}{A_2(\theta)} \quad (6)$$

The response function R can be computed from the respective spectrum outputs 220A, 220B of the respective segments 106A, 106B:

$$R = \frac{\sum_{j=1}^{N_{bins}} s_1(E_j) \cdot e^{-\mu(E_j)L} \Delta E_j}{\sum_{j=1}^{N_{bins}} s_2(E_j) \Delta E_j} = g(\theta) \quad (7)$$

The equation R=g(θ) can be solved to extract the tilt angle, θ. This is graphically illustrated in FIG. 9. As may be appreciated, the solution is not unique for symmetric g(θ) as the negative tilt angle also gives the same response. With respect to the graph of FIG. 9, this graph is representative of a misalignment response of a segmented pixel 102 misaligned with respect to an X-ray focal spot by a tilt angle θ. In this example, the graph includes an x-axis representing tilt angle θ and a y-axis representative of a ratio of counts in corresponding energy bins of the selected detector segments 106A, 106B to determine the misalignment tilt angle θ.

Figure 9:
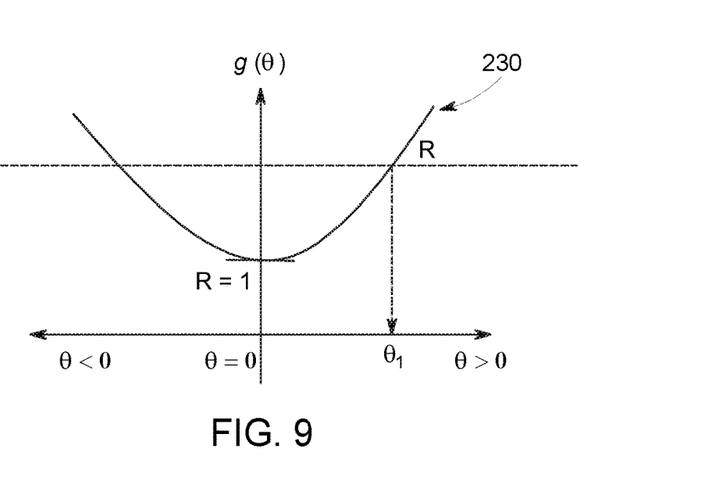
FIG. 9 depicts a graphical representation of gain in view of detector element tilt angle, in accordance with aspects of the present disclosure.

In conjunction with the graph, a curve 230 is depicted that represents a misalignment response. In one embodiment, the curve 230 may be retrieved from a look-up-table, or alternatively may be calculated on-the-fly. A tilt angle, e.g., θ₁, is obtained based on the photon count ratio using the curve 706. The tilt angle is provided may be provided as an input to the image reconstruction unit 118 of FIG. 1 for performing image calibration and generating a diagnostic image 142 based on the pixel outputs, which may be calibrated to take into account the corrected spectral response in view of the misalignment angle.

Figure 10:
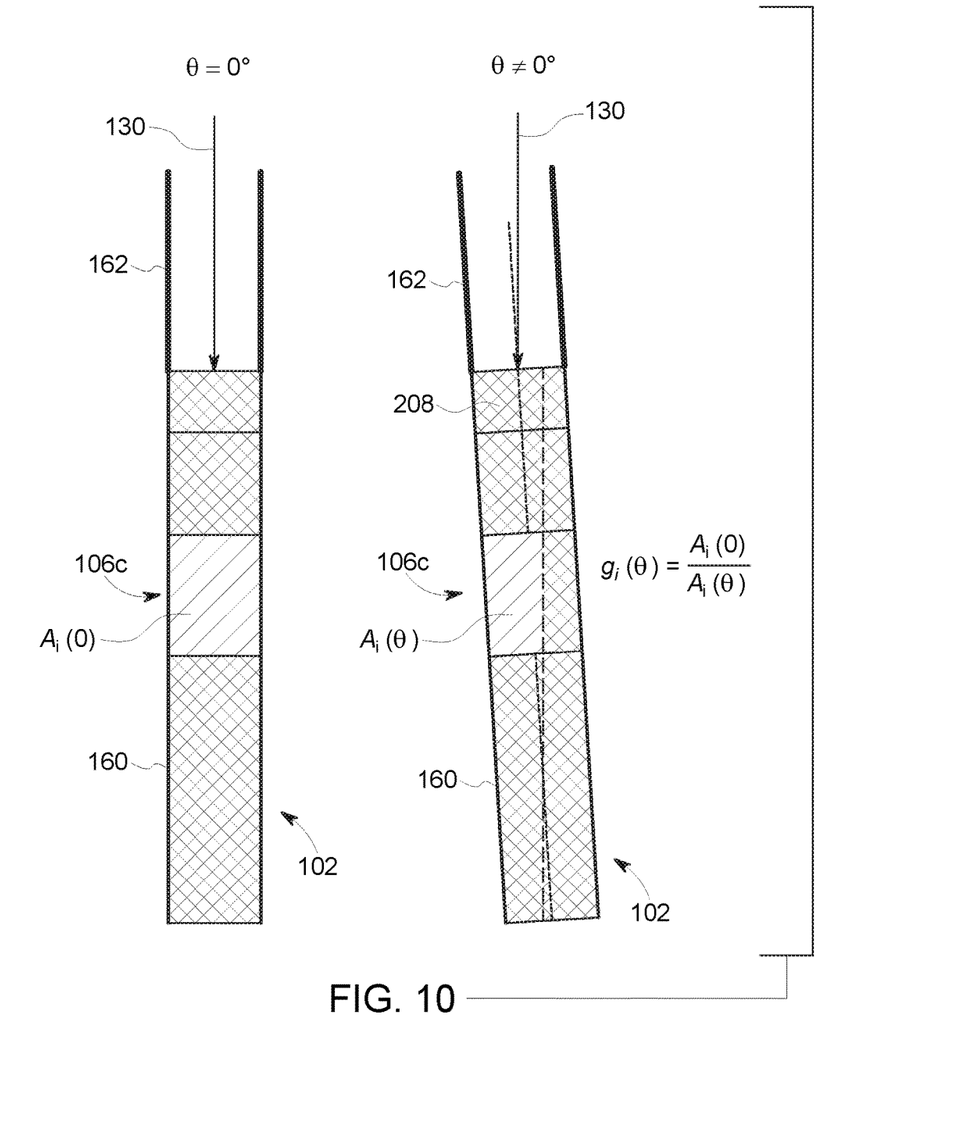
FIG. 10 depicts respective aligned and misaligned detector elements, in accordance with aspects of the present disclosure.

With respect to spectrum correction, one aspect the present approach employs an algorithm as generally discussed herein. By way of example, such an algorithm may estimate a misalignment tilt angle θ as described above. Gain factors $g_i(\theta)$, i=1, ... $N_{segment}$ are then computed that represent the loss of signal in each vertical segment 106 of a pixel 102 due to tilt, as shown in FIG. 10, where the segment 106C of a pixel 102 is depicted in an aligned state (leftmost figure) and an misaligned state (rightmost figure), with a corresponding loss of signal area depicted in the misaligned state. The gain factors to address such misalignment may be given by:

$$g_i(\theta) = \frac{A_i(\theta)}{A_i(\theta)} \quad (8)$$

As noted above, a correction to the estimated spectrum for each segment is applied based upon these gain factors, such as in accordance with:

$$s_i'' = g_i \cdot s_i' \quad (9)$$

where $s_i'$ is the measured spectrum in segment i. Based upon the corrected segment spectra, the corrected spectrum for a given pixel 102 may be computed, such as by:

$$\hat{s}(E_j) = \sum_{i=1}^{N_{segment}} s_i''(E_j) = \sum_{i=1}^{N_{segment}} g_i(\theta) \cdot s_i'(E_j) \quad (10)$$

The corrected pixel spectra may then be used in image reconstruction as discussed herein.

Figure 11:
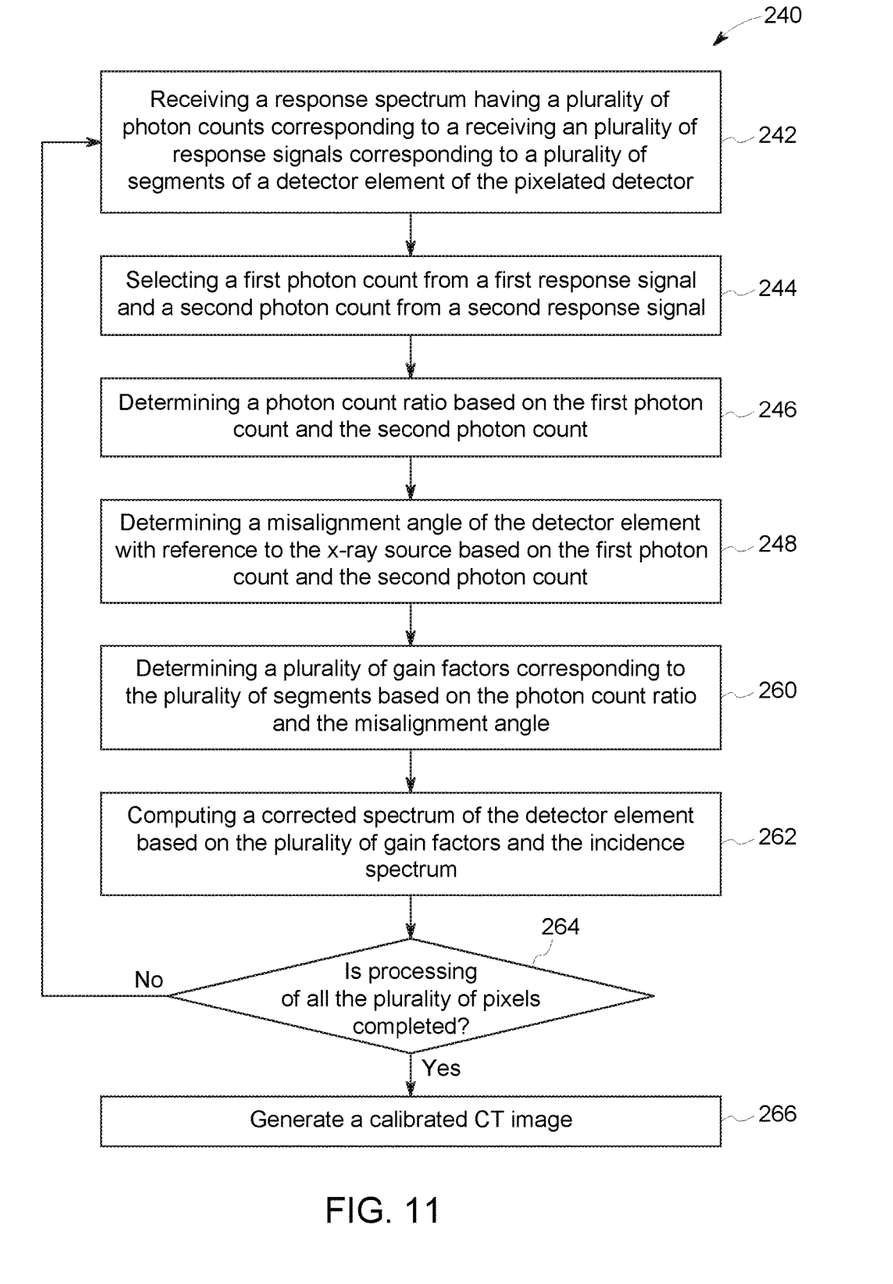
FIG. 11 is a flow chart of a method for self-calibration of computed tomography (CT) image, in accordance with aspects of the present disclosure.

With the preceding in mind, FIG. 11 is a flow chart illustrating a method 240 for self-calibration of a CT image, in accordance with aspects of the present specification. At step 242, the method includes receiving a plurality of response signals corresponding to a plurality of segments 106 of a detector element 102 of the pixelated detector 98, where different response signals generated for a given detector element correspond to photon counts for different energy bins. At step 244, the method includes selecting a first photon count from a first response signal and a second photon count from a second response signal, where the first photon count and the second photon count corresponds to a same energy bin among the plurality of energy bins. The method may also include determining a photon count ratio based on the first photon count and the second photon count at step 246. At step 248, the method also includes determining a misalignment angle of the detector element with reference to the X-ray source based on the first photon count and the second photon count. Further at step 260, the method includes determining a plurality of gain factors corresponding to the plurality of segments based on the photon count ratio and the misalignment angle. The method also includes computing a corrected spectrum corresponding to the detector element based on the plurality of gain factors and the plurality of response signals at step 262.

At step 264, availability of the corrected spectrum signals for all the plurality of pixels is verified. If the processing of the plurality of pixels is completed, generation of a calibrated image is initiated. However, if the processing of one or more of the plurality of pixels is not completed, the control is passed to step 242 for processing the remaining pixels, and the steps 242, 244, 246, 248, 260, 262 are repeated to generate a plurality of corrected spectrum signals corresponding to the plurality of pixels. If the processing of the plurality of pixels is completed, at step 266, the method further includes generating a calibrated CT image based on the plurality of corrected spectrum signals. In the calibrated CT image generated using the steps of the method 240, the artifacts due to the detector misalignment with the radiation signal is compensated. In one embodiment, generating the calibrated CT image includes generating a plurality of corrected spectrum signals corresponding to each view angle among a plurality of view angles. Further, generating the calibrated CT image includes reconstructing a plurality of sub-images corresponding to the plurality of view angles, wherein each of the plurality of sub-images is re-constructed based on the plurality of corrected spectrum signals corresponding to each view angle. The calibrated CT image is generated based on the plurality of sub-images corresponding to the plurality of view angles.

With the preceding in mind, it may be noted that implementation of the present calibration algorithm may vary depending on the operational context. By way of example, in contexts where it is known or expected that calibration does not change during a scan operation, the calibration may be performed prior to or after the scan is performed to obtain the correction factors used in image reconstruction. Likewise, if alignment of the detector pixels and X-ray focal spot varies with rotation speed, calibrations may be performed for different rotation speeds (such as one set of calibration factors for each rotation speed of operational interest) and these calibration factors may be stored for subsequent correction steps. Similarly, when alignment is known or expected to be view (i.e., view angle) dependent, calibration factors may be obtained and stored for each view angle. It may also be noted that the size of the calibration layer (i.e., segments) may differ. In accordance with the present approach, this may also be accounted for by the calibration factors generated in accordance with the present approach. Lastly, it may be appreciated that the signal-to-noise ratio (SNR) for scan operations may be improved by averaging data from pixels 102 within the same sensor slab.

Various systems and methods for self-calibration of CT detectors disclosed herein detect misalignment of the detector during the scan and perform calibration in real-time by signal processing techniques. The technique provided here make the detector more robust to changes against temperature and focal spot movements. The diagnostic image generated by energy resolving calibrated response signals is able to present enhanced features compared to conventional CT based diagnostic images. Advantageously, the segmented detector employed in the self-calibration technique may also be used to correct effect of pile-up and scatter artifact signals on the quality of resulting CT image.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method for calibrating an energy resolving computed tomography (CT) system comprising an X-ray source and a pixelated detector, the method comprising:
for each respective segment of a detector element comprising a plurality of segments, acquiring a respective response signal, wherein each response signal comprises a plurality of photon counts each corresponding to a different energy bin of the respective segment;
for the detector element, determining a first photon count for an energy bin of a first segment and a second photon count for the same energy bin of a second segment, wherein the first segment and the second segment are vertically offset within the respective detector element;
determining a photon count ratio based on the first photon count and the second photon count;
determining a misalignment angle of the detector element with reference to the X-ray source based on the photon count ratio;
determining a plurality of gain factors for the plurality of segments of the detector element based on the photon count ratio and the misalignment angle; and
determining a corrected spectrum for the detector element using the plurality of gain factors and the response signals.

2. The method of claim 1, wherein the pixelated detector comprises a plurality of detector elements and wherein a respective corrected spectrum is calculated for some or all detector elements of the pixelated detector.

3. The method of claim 2, wherein the dimensions of the detector elements are approximately 0.5 mm ×0.5 mm along a planar surface of the pixelated detector facing the X-ray source and between about 20 mm to about 80 mm in a direction of X-ray propagation.

4. The method of claim 1, wherein the detector element comprises a strip of semiconductor material segmented into the plurality of segments, wherein the segments increase in thickness as distance from the X-ray source increases.

5. The method of claim 1, wherein the corrected spectrum is determined in substantially real-time during a clinical scan operation.

6. The method of claim 1, wherein the gain factors are determined prior to a clinical scan operation and used to correct the spectra of data acquired during the clinical scan operation.

7. The method of claim 1, comprising:
acquiring different gain factors for different rotational speeds of the X-ray source and pixelated detector;
wherein determining the corrected spectrum for the detector element uses the gain factors corresponding to the rotational speed at which spectral data was acquired.

8. The method of claim 1, comprising:
acquiring different gain factors for different view angles of the X-ray source and pixelated detector with respect to an imaged volume;
wherein determining the corrected spectrum for the detector element uses the gain factors corresponding to the view angle at which spectral data was acquired.

9. A computed tomography (CT) imaging system, comprising:
an X-ray radiation source configured to emit X-ray radiation;
a pixelated detector configured to generate signals in response to the emitted X-ray radiation, wherein the pixelated detector comprises a plurality of detector elements, each detector element comprising a plurality of segments offset in the direction of X-ray radiation propagation;
a readout channel for each segment of each detector element, wherein each readout channel, during operation, generates a photon count for each bin in a plurality of energy bins;
a calibration sub-system configured to, based upon the photon counts for a first segment and a second segment of a respective detector element:
determine a first photon count for an energy bin of the first segment and a second photon count for the same energy bin of the second segment, wherein the first segment and the second segment are vertically offset within the respective detector element;
determine a photon count ratio based on the first photon count and the second photon count;
determine a misalignment angle of the respective detector element with reference to the X-ray radiation source based on the photon count ratio;
determine a plurality of gain factors for the plurality of segments of the respective detector element based on the photon count ratio and the misalignment angle; and determine a corrected spectrum for the respective detector element using the plurality of gain factors and the response signals;

an image reconstruction unit configured to generate an output image using the respective corrected spectra of some or all of the detector elements.

10. The CT imaging system of claim 9, wherein the X-ray radiation source comprises an X-ray tube.

11. The CT imaging system of claim 9, wherein each detector element comprises a strip of semiconductor material segmented into the plurality of segments, wherein the segments increase in thickness as distance from the X-ray radiation source increases.

12. The CT imaging system of claim 9, wherein the dimensions of the detector elements are approximately 0.5 mm×0.5 mm along a planar surface of the pixelated detector facing the X-ray radiation source and between about 20 mm to about 80 mm in a direction of X-ray radiation propagation.

13. The CT imaging system of claim 9, wherein the corrected spectra are stored on a memory unit of the CT imaging system for use in imaging operations subsequent to the calibration operation used to generate the corrected spectra.

14. One or more non-transitory computer-readable media storing processor-executable instructions that, when executed by one or more processors, cause the one or more processors to perform acts comprising:

for each respective segment of a detector element comprising a plurality of segments, acquire a respective response signal, wherein each response signal comprises a plurality of photon counts each corresponding to a different energy bin of the respective segment;

for the detector element, determine a first photon count for an energy bin of a first segment and a second photon count for the same energy bin of a second segment, wherein the first segment and the second segment are vertically offset within the respective detector element;

determine a photon count ratio based on the first photon count and the second photon count;

determine a misalignment angle of the detector element with reference to an X-ray source based on the photon count ratio;

determine a plurality of gain factors for the plurality of segments of the detector element based on the photon count ratio and the misalignment angle; and determine a corrected spectrum for the detector element using the plurality of gain factors and the response signals.

15. The one or more non-transitory computer-readable media of claim 14, wherein the processor-executable instructions, when executed, calculate corrected spectra for some or all detector elements of a pixelated detector.

16. The one or more non-transitory computer-readable media of claim 14, wherein the processor-executable instructions, when executed, determine the corrected spectra in substantially real-time during a clinical scan operation.

17. The one or more non-transitory computer-readable media of claim 14, wherein the processor-executable instructions, when executed, determine the gain factors prior to a clinical scan operation and use the gain factors to correct the spectra of data acquired during the clinical scan operation.

18. The one or more non-transitory computer-readable media of claim 14, wherein the processor-executable instructions, when executed:

acquire different gain factors for different rotational speeds of the X-ray source and pixelated detector;

wherein determining the corrected spectrum for the detector element uses the gain factors corresponding to the rotational speed at which spectral data was acquired.

19. The one or more non-transitory computer-readable media of claim 14, wherein the processor-executable instructions, when executed:

acquire different gain factors for different view angles of the X-ray source and pixelated detector with respect to an imaged volume;

wherein determining the corrected spectrum for the detector element uses the gain factors corresponding to the view angle at which spectral data was acquired.

* * * * *